United States Patent
Rosenblum et al.

(10) Patent No.: US 7,223,397 B1
(45) Date of Patent: May 29, 2007

(54) POTENTIATION OF ANTI-CD38-IMMUNOTOXIN CYTOTOXICITY

(75) Inventors: Michael Rosenblum, Sugar Land, TX (US); Kapil Mehta, Houston, TX (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 09/226,895

(22) Filed: Jan. 7, 1999

(51) Int. Cl.
*A61K 39/00* (2006.01)
*A01N 31/04* (2006.01)

(52) U.S. Cl. .............................. 424/178.1; 424/183.1; 514/725

(58) Field of Classification Search ............. 424/183.1; 530/391.7
See application file for complete search history.

(56) References Cited

OTHER PUBLICATIONS

Meridith et al, "Phase II Study of Dual 131-I Labeled Monoclonal Anitbody Therapy with Interferon in Patients with Metastatic Colon Cancer", Clinical Cancer Research, vol. 2, pp. 1811-1818, 1996.*
Mehta et al, "Retinoic acid-induced CD38 cell surface protein as a target for immunotoxin therapy: In vitro evaluation." Proceedings of the American Association for Cancer Research, vol. 38, p. 88, 1997.*
Hirota et al, "Suppression of an Epidermal Growth Factor Receptor-hyperproducing Tumor by an Immunotoxin Conjugate of Gelonin and a Monolonal Anti-Epidermal Growth Factor Receptor Anitbody." Cancer Research, vol. 49, pp. 7106-7109, 1989.*
Mehta et al, "Introduction of CD39 by Retinoic Acid in Myeloid Leukemia Cells." Proceedings of the American Association for Cancer Research, vol. 35, p. 92, 1996.*
Flavell et al, "Systemic therapy with 3BIT, a triple combination cocktail of . . . anti CD38-saporin immunotoxin", Cancer Research, vol. 57, pp. 4824-4829, Nov. 1997.*
abstract of Zhao et al (Blood, 1994, vol. 84, No. 10, suppl 1, p. 54A).*
Scholm ('Monoclonal Antibodies They'reMore and Less Than You Think', In: Molecular Foundations of Oncology, 1993, S. Broder, Ed, pp. 95-134).*
Drach (Cancer Research, 1994, vol. 54, pp. 1746-1752).*
Goldmacher et al (Blood, 1994, vol. 84, pp. 3017-3025).*
O'Connor et al (Blood, vol. 86, pp. 4286-4294).*
Jacquelyn A. Hank, et al. *Clinical and Immunological Effects of Treatment with Murine Anti-CD3 Monoclonal Antibody along with Interleukin 2 in Patients with Cancer.* Clinical Cancer Research, vol. 1, pp. 481-491 (May 1995).

* cited by examiner

*Primary Examiner*—Karen A Canella
(74) *Attorney, Agent, or Firm*—Fulbright & Jaworski L.L.P.

(57) ABSTRACT

The present invention is directed to the use of agents that induce high levels of cell surface molecules to provide targets for immunotoxins directed against the same cell surface molecules. A specific example is given in which all-trans-retinoic acid (RA) is used to induce high levels of CD38 cell surface antigen expression in several myeloid and lymphoid leukemia cells. CD38 was then used as target for delivering plant toxin (gelonin) to leukemia cells. Treatment of leukemia cells with RA induced high levels of CD38 in those cells that otherwise had low CD38 expression. The RA-induced leukemia cells then became exquisitely sensitive to an immunotoxin constructed from an anti-CD38 monoclonal antibody conjugated to the plant toxin gelonin.

10 Claims, 9 Drawing Sheets

MoAb-based therapy of Cancer: CD38 expression in normal human tissues

Legend: Master blot from Clontech was hybridized with radiolabeled human CD38-specific nucleic acid probe. Only the thymus tsisue (from adult and fetal) showed mRNA transcript for CD38. Prostate was also positive but to a lesser extent.

MoAb-based therapy of Cancer: Reversal effect of unconjugated anti-CD38 moAb on IT-induced cytotoxicity in HL-60 cells

Legend: HL-60 cells were incubated
With IT alone (C) or IT+RA (5nM)
In presence or absence of increasing
Concentrations unconjugated anti-
CD38 moAb. Cell viability was
Tested fter 3 days incubation by
using MTS assay

MoAb-based therapy of Cancer:

IT-induced killing of Doxo-resistant HL-60 cells

Legend: HL-60 subcloned cells, resistant to Adriamycin-induced killing were cultured with IT alone in the presence of 5 nM RA. After 3 days incubation, cells viability was tested using MTS assay.

MoAb-based therapy of Cancer:
IT-mediated killing of MZ (NHL) cells

Legend: A non-Hodgkin lymphoma cell line that has a high basal expression of CD38 antigen was incubated with IT in presence or absence of RA. The cell cell viability was checked after 3 days culture using MTS assay.

Legend: An HL-60 subclone with mutated RARalpha gene that renders these cells resistant to RA-induced CD38 expression, was cultured with IT alone or in presence of 5 mM RA. After 3 days the cell viability was determined using MTS assay.

POTENTIATION OF ANTI-CD38-IMMUNOTOXIN CYTOTOXICITY

BACKGROUND OF THE INVENTION

1. Field of the Invention

The present invention relates generally to the fields of immunology and tumor biology. More specifically, the present invention relates to treatment for the enhancement of CD38 protein expression in target tumor cells to increase the cytotoxicity of anti-CD38 based immunotoxins.

2. Description of the Related Art

The use of monoclonal antibodies for delivering drugs or toxins to distinct molecular structures expressed on the surface of unwanted tumor cells represents an attractive and potentially useful strategy. Theoretically, such a targeted approach to cancer therapy could offer a major advance in the selective elimination of tumor cells while reducing the toxicity of treatment towards normal non-target tissues. Nevertheless, in practice many problems exist that need to be addressed before immunotoxin or antibody-drug therapies can be truly effective in vivo.

One potential limitation to the success of any targeted approach to therapy is the heterogeneity of target antigen expression within a population of tumor cells. It follows that if a small number of cells within a tumor were negative for the target antigen or expressed the antigen only very weakly, then these cells could possibly escape destruction due to a failure of antibody-mediated delivery of the cytotoxic agent to those particular cells. A possible means of overcoming this problem would be to identify agents that induce high levels of cell surface target molecules, in the expectation that target tumor cells which were antigen negative would express these target molecules in abundance.

All-trans-retinoic acid (RA) is an agent that induces high levels of CD38 cell surface antigen expression in several myeloid and lymphoid leukemia cells. Retinoic acid-induced expression of CD38 in these cells is specific, rapid, dose-dependent, and highly sensitive, with 4-fold induction at as low a dose of retinoic acid as $10^{-13}$ M. The induction of CD38 expression by retinoic acids has been shown to involve the RARα retinoid receptor. RAR receptors form heterodimers with RXR receptors; the RXR/RAR heterodimer then interacts with DNA sequences known as retinoic acid response elements (RARE's) which are involved in retinoid-induced transcription.

CD38 is a 45-kDa cell surface protein which is primarily expressed by early progenitor and mature activated cells of the hematopoetic system. It is a transmembrane glycoprotein with a short N-terminal cytoplasmic domain and a long C-terminal extracellular domain. The extracellular domain has been shown to be a bifunctional enzyme having ADP-ribosyl cyclase as well as ADP-ribosyl hydrolase activities in that it catalyzes the conversion of NAD+ to cADPR (cyclase) and can further hydrolyze it to ADP-ribose (hydrolase). cADPR is involved in the mobilization of calcium from intracellular stores which is a second messenger activity important for cellular proliferation, differentiation, and apoptosis. CD38 is believed to act as a receptor for an unidentified ligand and to act as a cell adhesion molecule by interacting with CD31. Experiments in which CD38 function was activated by monoclonal antibodies directed against it have implicated CD38 in proliferation of mature B lymphocytes and myeloid leukemia cells, rescue of germinal center cells from apoptosis, and growth suppression of stroma-supported cultures of B-cell progenitors as well as induction of the cytokines IL-6, IGN-g, GM-CSF, and IL-10. In addition, it has been shown to signal an increase in TNF-α, IL-1, IL-6, and IL-8 transcription in myeloid leukemia cells.

The prior art is deficient in the lack of a method to induce the expression of a target molecule for immunotherapy of tumor and other disease-causing cells. The present invention fulfills this longstanding need and desire in the art.

SUMMARY OF THE INVENTION

The present invention demonstrates the potential of retinoid-induced CD38 expression to serve as a target for delivering the immunotoxin anti-CD38-gelonin. The results obtained suggested that retinoic acid treatment of leukemia cells, even at very low concentrations (subnanomolar) makes these cells exquisitely sensitive to immunotoxin-induced killing.

The current invention comprises a method of treating an individual having a pathophysiological state, comprising the step of administering to said individual a pharmacologically effective dose of an agent which upregulates the expression of a cellular target and also administering a pharmacologically effective dose of an immunotoxin directed against the upregulated cellular target.

The current invention also comprises a method of treating an individual having a pathophysiological state responsive to retinoid treatment, comprising the step of administering to said individual a pharmacologically effective dose of a retinoic acid metabolite and a pharmacologically effective dose of an immunotoxin.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

An immunotoxin is defined as any immunological molecule such as an antibody which has been conjugated with a toxin, preferably a cytotoxin.

The present invention is directed to a method of treating an individual having a pathophysiological state, comprising the step of administering to said individual an a pharmacologically effective dose of an agent which upregulates the expression of a cellular target. This administration is followed by the administration of a pharmacologically effective dose of an immunotoxin directed against the cellular target. Preferably, the administered agent is selected from the group consisting of differentiating agents, cytokines, interleukin-2, tumor necrosis factor, interferon-α, interferon-γ and peptide hormones.

In one embodiment, the invention comprises the administration of a pharmacologically effective dose of a retinoid. Preferably, the retinoid induces expression of CD38 antigen in cells. If this is the case, a pharmacologically effective dose of a anti-CD38 immunotoxin is administered. Representative pathophysiological states which may be treated using the methods of this embodiment of the invention include RARα selective acute myeloid leukemia, acute promyelocytic leukemia, lymphomas, and myelomas.

Representative retinoic acid metabolites which may be used in the methods of the present invention include all-trans-retinoic acid (RA); 9-cis retinoic acid (9-cis RA); (E)-4-[2-(5,6,7,8-tetrahydro-5,5,8,8-tetramethyl-2-naphthalenyl)-1-propenyl]benzoic acid (TTNPB); (E)-4-[2-(5,6,7,8-tetrahydro-3,5,5,8,8-pentamethyl-2-naphthalenyl)-1-propenyl]benzoic acid (3-met TTNPB); and other retinoids that can bind and activate the RARα receptor. Preferably, the retinoid is administered in a dose of from about 0.1 mg/kg to about 2 mg/kg.

The immunotoxin used in the methods of the present invention specifically target cells expressing the CD38 antigen. Preferably, the immunotoxin comprises a monoclonal antibody directed against the CD38 antigen conjugated to a toxin molecule. Although a person having ordinary skill in this art could substitute any toxin, a preferred toxin useful in these methods is gelonin. Although a person having ordinary skill in this art could substitute any monoclonal antibody specific for the CD38 antigen, IB4 or IB6 antibodies were used herein to demonstrate the present methods. Preferably, the immunotoxin is administered in a dose of from about 0.05 mg/kg to about 2 mg/kg.

The following examples are given for the purpose of illustrating various embodiments of the invention and are not meant to limit the present invention in any fashion.

EXAMPLE 1

CD38 Expression in Normal Tissues is Limited Mainly to the Thymus.

Figure 1:
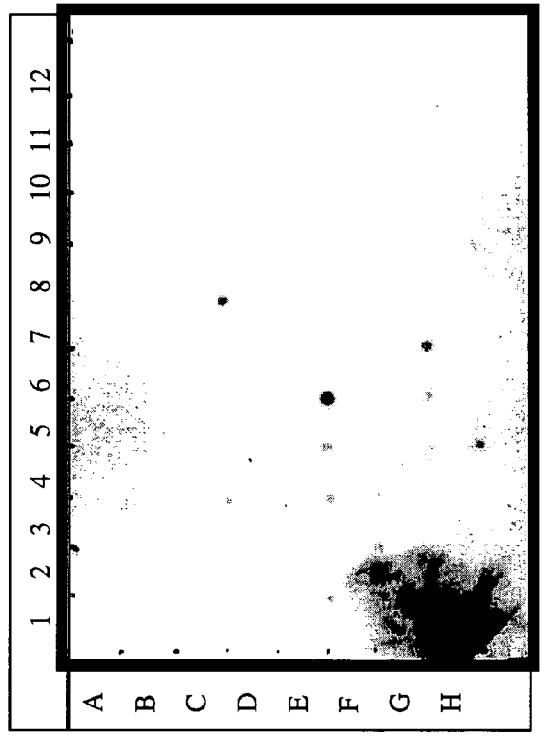
FIG. 1 shows a dot blot of mRNA from a variety of human tissues after hybridization with a radiolabeled human CD38-specific nucleic acid probe. Relatively low CD38 mRNA expression was observed only in thymus tissue [from both adult (E5) and fetal (G6)] while a lesser level of expression was seen in normal prostate (C7).

The tissue specificity of CD38 was examined by the hybridization of a radiolabeled CD38 nucleic acid probe against a commercial (CLONTECH) tissue specific mRNA dot blot. The results of the hybridization are shown in FIG. 1. It was observed that CD38 is mainly expressed in the thymus with significantly lower levels of expression in the prostate.

EXAMPLE 2

Retinoic Acid (RA) Augments the Cytotoxic Effect of Immunotoxin Through Enhanced Expression of CD38.

Figure 2:
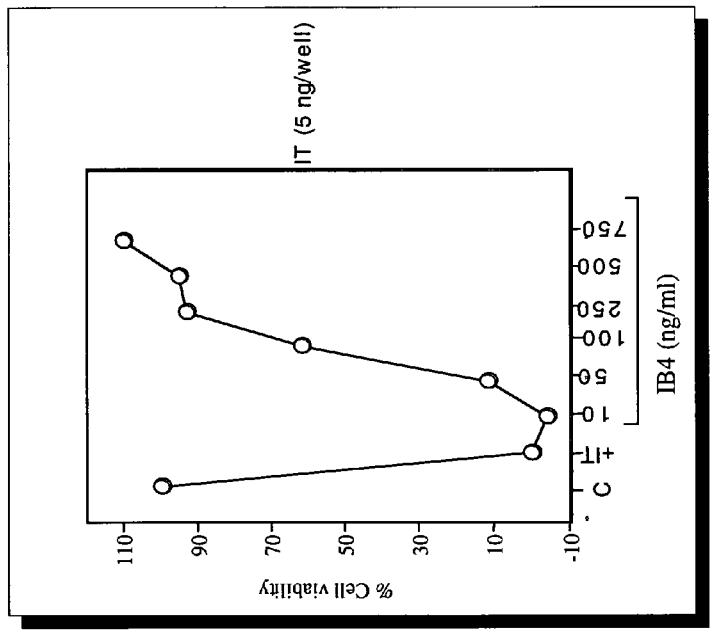
FIG. 2 shows the effects of 5 nM all-trans-retinoic acid (RA) on the cytotoxicity of the immunotoxin and the effects of adding increasing concentrations of the unconjugated anti-CD38 monoclonal antibody (IB4). Point C indicates the effect of immunotoxin alone. +IT (+RA) shows the effect of 5 nM all-trans-retinoic acid (RA) on the cytotoxicity of the immunotoxin. In the rest of the samples, increasing concentrations of IB4 were added along with immunotoxin and 5 nM all-trans-retinoic acid (RA). After 3 days of incubation, cell viability was determined with the MTS assay. The results are represented in terms of % surviving cells.

HL-60 cells were incubated with either immunotoxin alone or in the presence of 5 nM retinoic acid (RA). Increasing concentrations of unconjugated IB4 monoclonal antibody were added to the cells incubated with immunotoxin and retinoic acid. After three days, the cells were assayed for viability with the MTS assay. Briefly, 6.5 mg/ml MTS solution [(3-(4,5-dimethylthiazol-2-yl)-5-(3-carboxymethoxyphenyl)-2-(4-sulfophenyl)-2H-tetrazolium] and 0.5 mM PMS (phenazine methosulfate) solution were mixed at a ratio of 20:1. 20 µl of the combined MTS/PMS solution was placed in each well of a 96 well plate containing samples of the cells to be tested. The plate was incubated for 1–4 hours at 37° C. in a 5% $CO_2$ atmosphere, after which time, the amount of formazan produced by live cells from cellular reduction of MTS was measured by reading the absorbance at 490 nm. The results are shown in FIG. 2.

Immunotoxin alone had little effect on the viability of the cells (C). However, when the cells were incubated with immunotoxin in the presence of 5 nM retinoic acid, a significant reduction in cell viability was observed. Increasing concentrations of unconjugated IB4 monoclonal antibody blocked the cytotoxic effect of immunotoxin and retinoic acid. The fact that unconjugated IB4 blocked the ability of the immunotoxin to kill the cells demonstrates that the immunotoxin is specifically interacting with the CD38 surface marker and that the effect of the retinoic acid is to increase the expression of the CD38 antigen.

EXAMPLE 3

All-Trans-Retinoic Acid (RA) Pretreatment Enhances the Induced Killing of HL-60 Cells.

Figure 3:
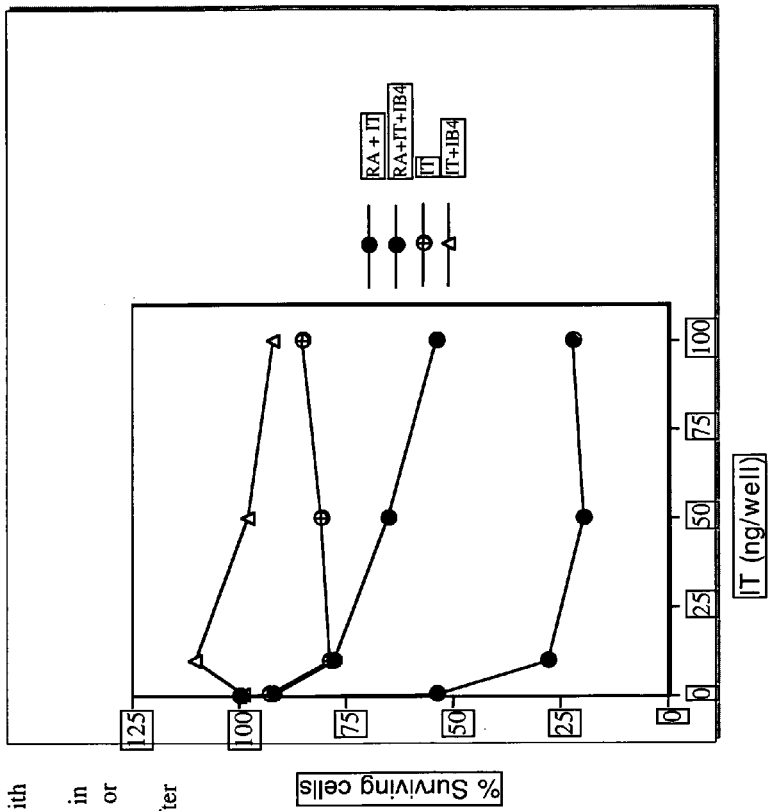
FIG. 3 shows effect of retinoic acid pretreatment on the cytotoxicity of anti-CD38 immunotoxin on HL-60 cells. HL-60 cells were incubated overnight in the presence or absence of retinoic acid. After removal of the media and twice washing the cells, the cells were reincubated with increasing concentrations of immunotoxin (represented as ng/well) in the presence or absence of 100-fold excess of unconjugated anti-CD38 monoclonal antibody IB4. After three days, the MTS assay was used to determine cell viability which is represented in terms of % surviving cells.

HL-60 cells were preincubated overnight in either the presence or absence of 5 nM all-trans-retinoic acid. The cells were washed twice and incubated in increasing concentrations of immunotoxin in either the presence or absence of IB4 unconjugated anti-CD38 MoAb. After three days, the cell were assayed for viability. The results are shown in FIG. 3.

Preincubation with all-trans-retinoic acid followed by immunotoxin treatment resulted in more cell death than treatment with immunotoxin alone. The presence of 100 fold excess of the unconjugated anti-CD38 monoclonal antibody IB4 blocked the toxicity of the immunotoxin in both cases by competing with the immunotoxin for access to the CD38 markers on the cells. These results demonstrate that the all-trans-retinoic acid (RA) was causing some change in the cells which render them more susceptible to the immunotoxin rather than playing a direct role in the death of the target cells.

EXAMPLE 4

Gelonin must be Conjugated to the Anti-CD38 Antibody to have a Toxic Effect on the Target Cells.

Figure 4:
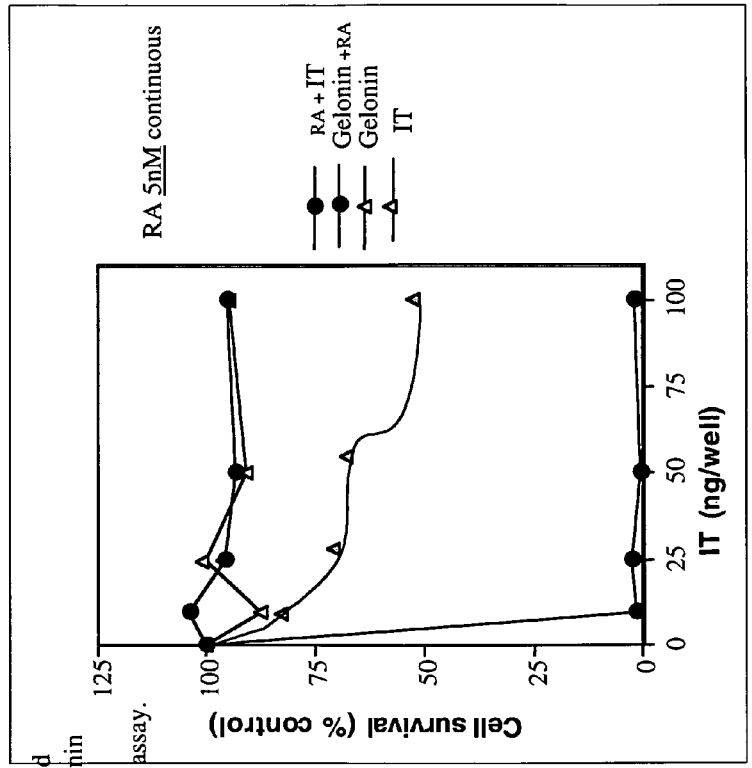
FIG. 4 shows the effect of treatment with either immunotoxin or gelonin on the viability of HL-60 cells. HL-60 cells were incubated for three days in increasing concentrations of either immunotoxin or gelonin (represented as ng/well toxin) in the presence or absence of 5 nM retinoic acid. Cell viability was determined by the MTS assay and is represented here in terms of percent cell survival relative to the control sample (no toxin).

HL-60 cells were incubated for three days with increasing concentrations of either immunotoxin or gelonin in either the presence or absence of 5 nM retinoic acid. Afterwards, the cells were assayed for viability using the MTS assay. As seen in FIG. 4, gelonin alone had no toxic effect in either the presence of absence of 5 nM. Thus, the toxic effect of gelonin depends on it being conjugated to the anti-CD38 monoclonal antibody in order to deliver the toxin to the cell.

EXAMPLE 5

Even Nominal Levels of All-Trans-Retinoic Acid (RA) Lead to Increased Toxicity of the Immunotoxin.

Figure 5:
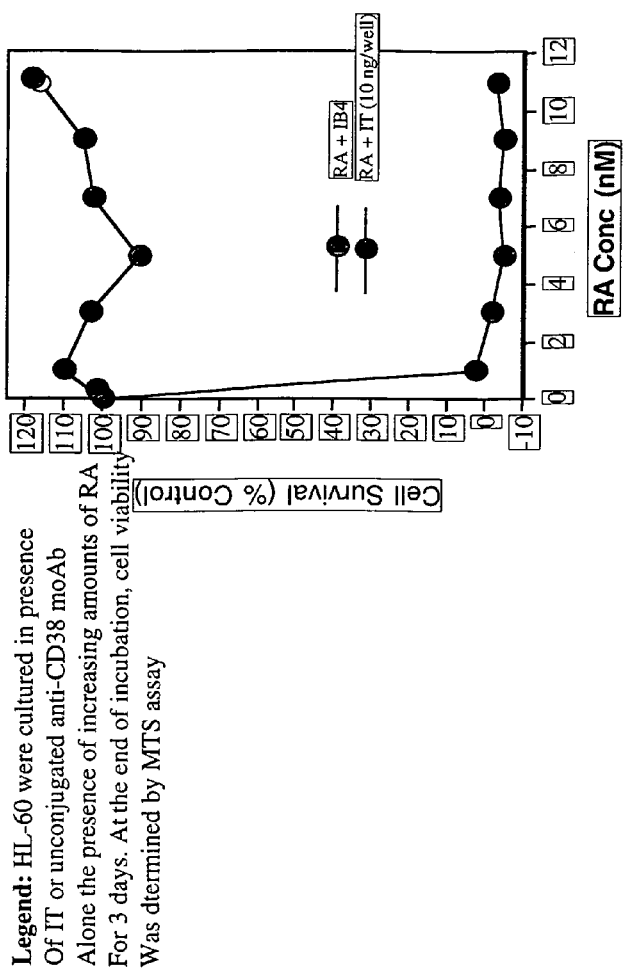
FIG. 5 shows the effect of increasing concentrations of all-trans-retinoic acid (RA) (in nM) on cell survival. HL-60 cells were incubated with either immunotoxin or unconjugated anti-CD38 monoclonal antibody in either the absence or the presence of increasing concentration of retinoic acid (shown in nM). After three days, cell viability was determined by MTS assay and is shown in terms of percentage of cell survival relative to an untreated control.

HL-60 were incubated with either immunotoxin or unconjugated IB4 monoclonal antibody in increasing concentrations of monoclonal antibody. FIG. 5 shows that even the lowest level of all-trans-retinoic acid (RA) (1 nM) lead to almost complete killing of the target cells by the immunotoxin. This effect was not observed with the unconjugated monoclonal antibody. This result indicates that it is the gelonin conjugated to the monoclonal antibody in the immunotoxin that leads to the increased cell death rather than some effect of the antibody itself.

EXAMPLE 6

Retinoic Acid can Induce Expression of the CD38 Marker in a Variety of Cell Lines.

Figure 6:
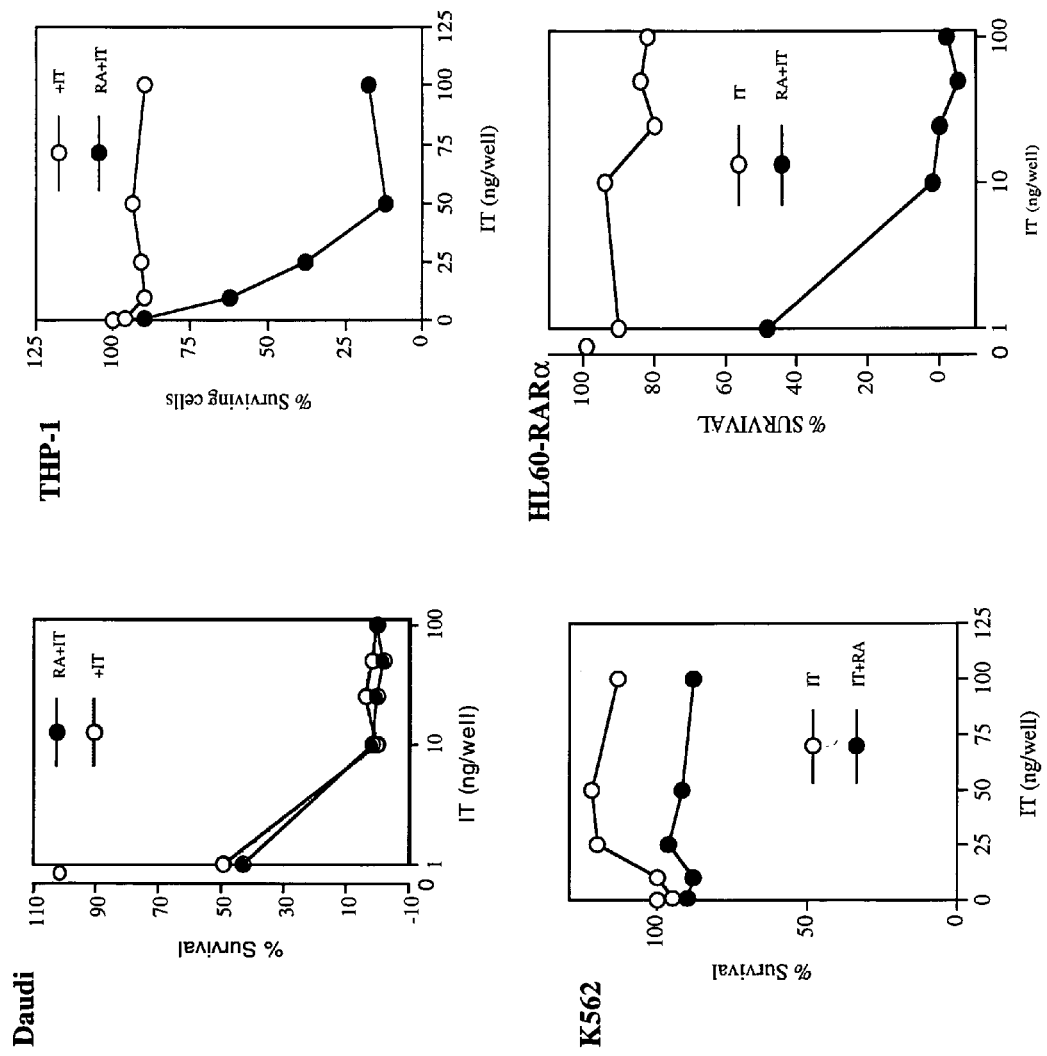
FIG. 6 shows the effect of increasing concentrations of immunotoxin (shown in ng/well) in either the presence or absence of 5 nM all-trans-retinoic acid (RA) on cell survival of different cell lines including (Daudi, THP-1, K562 (which is resistant to RA-induced expression of CD38), and a RARα-expressing variant of HL60. Cell viability was measured by the MTS assay after three days and is represented in terms of percent cell survival relative to an untreated control.

The Daudi, THP-1, K562, and HL60-RARα cell lines were treated with increasing concentrations of immunotoxin in either the presence or absence of 5 nM all-trans-retinoic acid (RA). After three days, the viability of the cells was examined using the MTS assay, which is shown in FIG. 6. In the THP-1 and HL60-RARα cell lines, all-trans-retinoic acid induced cell death while the cell which were cultured in the absence of all-trans-retinoic acid were mostly unaffected by the immunotoxin. In the Daudi cells, which have a high basal expression of CD38, the immunotoxin resulted in almost complete cell death regardless of whether retinoic acid was present. On the other hand, K562, which are resistant to RA-induced CD38 expression, were unaffected by the immunotoxin regardless of the presence of retinoic acid.

EXAMPLE 7

Immunotoxin Induced Cell Death in HL-60 Cells Resistant to Adriamycin.

Figure 7:
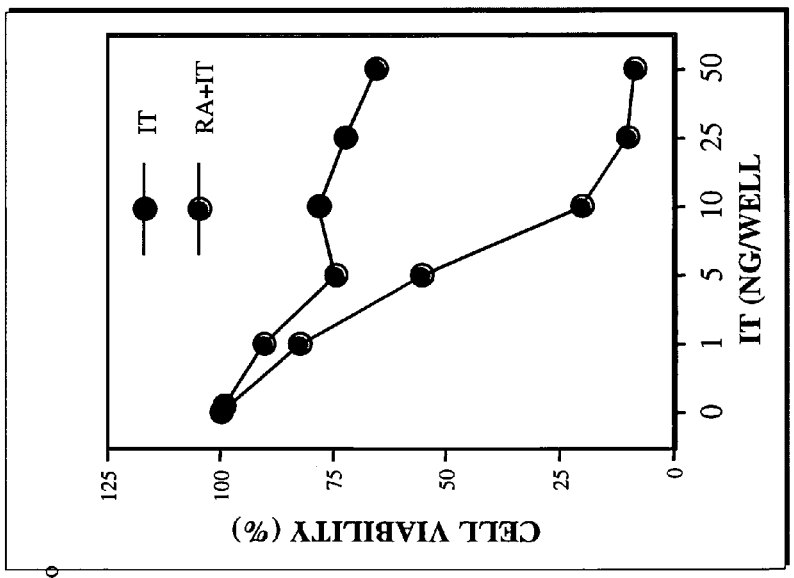
FIG. 7 shows the immunotoxin induced killing of Doxo-resistant HL-60 cells which are resistant to adriamycin-induced killing. The cells were incubated with increasing concentrations of immunotoxin (shown in ng/well) in either the presence or absence of 5 nM RA. Cell survival was assayed after 3 days using the MTS assay.

HL-60 subcloned cells, resistant to adriamycin-induced killing were cultured with immunotoxin either alone or in the presence of 5 nM all-trans-retinoic acid. After three days, the MTS assay was used to test cell viability. FIG. 7 shows the results obtained. Some cell death was observed in the presence of immunotoxin alone which was greatly augmented by the addition of 5 nM all-trans-retinoic acid.

EXAMPLE 8

Cells which have High Basal Expression of CD38 are Killed by Immunotoxin Regardless of the Presence or Absence of All-Trans-Retinoic Acid (RA).

Figure 8:
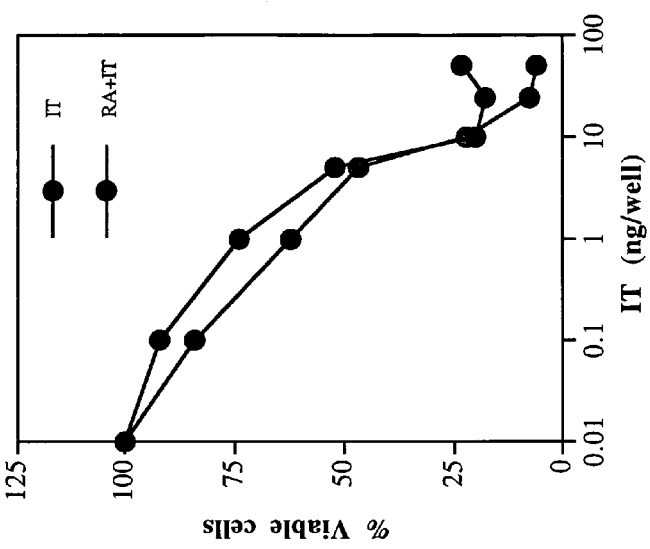
FIG. 8 shows the immunotoxin mediated killing of the non-Hodgkin lymphoma cell line MZ(NHL) that has a high basal expression of CD38 antigen. The cell were incubated with increasing concentrations of immunotoxin (shown in ng/well) in the presence or absence of 5 nM retinoic acid. After three days, cell viability was assayed with the MTS assay and is shown in terms of % viable cells.

MZ, a non-Hodgkin lymphoma cell line which has a high basal expression of CD38, was treated with increasing amounts of immunotoxin in either the presence or absence of 5 nM all-trans-retinoic acid. The addition of immunotoxin resulted in a high level of cell death regardless of the presence or absence of retinoic acid (FIG. 8). This is strong evidence that retinoic acid is increasing the toxicity of immunotoxin by enhancing the level of CD38 on other cell lines which do not have a high basal level of CD38.

EXAMPLE 9

Retinoic Increases CD38 Expression in a Number of Lymphoid Tumor Cells.

Table I lists the potential targets for anti-CD38 bound toxin treatment A number of different lymphoid tumor cell lines were treated with 5 nM all-trans-retinoic acid (RA). Afterwards, the expression of CD38 in untreated versus treated cell was measured by flow cytometry. A significant rise in CD38 expression was observed in acute myeloid leukemia (AML), acute promyelocytic leukemia (APL), lymphoma, and myeloma tumor cells. The increase in CD38 expression ranges from 2.5 to 20 fold. Thus, retinoic acid can be used in all of these tumor types to increase the vulnerability of the tumor cells to immunotoxin treatment.

EXAMPLE 10

Immunotoxin does not Affect Cells Resistant to All-Trans-Retinoic Acid (RA)

Figure 9:
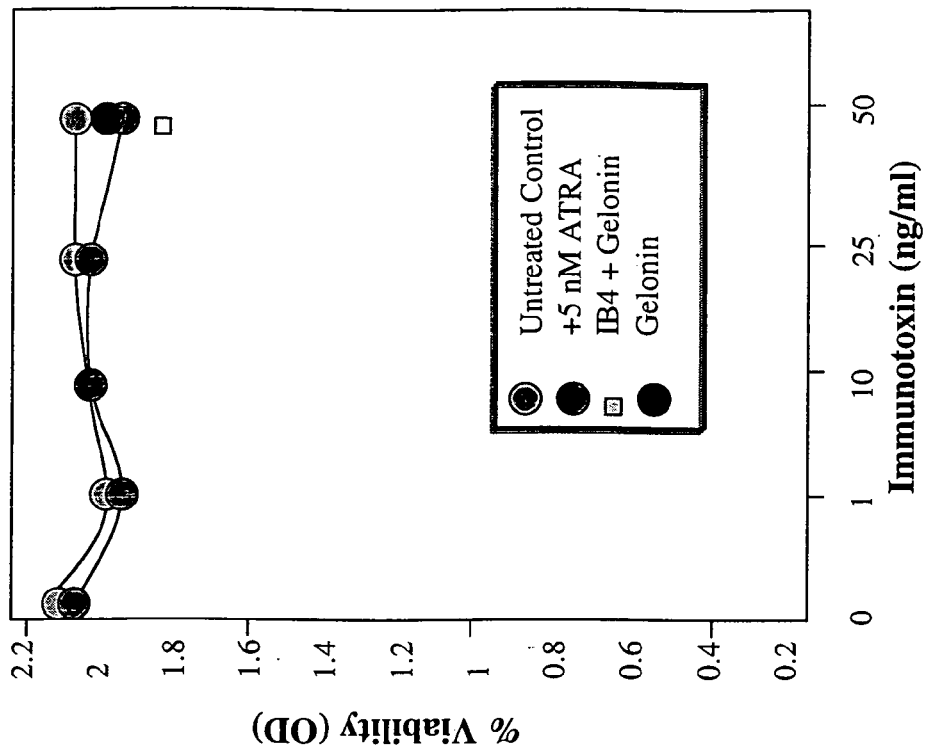
FIG. 9 shows the immunotoxin mediated killing of the retinoic acid-resistant variant of the HL60 cell line (HL60R). These cells are resistant to retinoic acid-induced expression of the CD38 antigen due to a point mutation in the retinoic acid receptor alpha (RARα) gene. The cell line was cultured with increasing concentrations of immunotoxin (in ng/ml) under different conditions. After 3 days, cell viability was assayed by the MTS assay and is represented in terms of O.D. The presence of retinoic acid failed to promote immunotoxin-induced killing of these cells due to their inability to express CD38 antigen in response to retinoic acid treatment.

HL-60 cells with a mutated RARα gene that renders the cells resistant to the effects of retinoic acid were treated with immunotoxin in either the presence or absence of 5 nM retinoic acid. In these cells, the addition of retinoic acid had no effect on the toxicity of the immunotoxin. As shown in FIG. 9, no appreciable cell death was observed in the cells treated with all-trans-retinoic acid (RA), with unconjugated IB4 and gelonin, or with gelonin alone. This is further proof that the immunotoxin kills cells which are affected by retinoic acid because of a retinoid induced increased in expression of CD38 target of the immunotoxin.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

TABLE 1

Potential targets for anti-CD38 bound toxin treatment

| Cell target | Basal CD38 | CD38 after RA treatment |
| --- | --- | --- |
| AML | 50 ± 10 | 180 ± 20 |
| APL | 6 ± 4 | 120 ± 30 |
| Lymphomas | 80 ± 20 | 210 ± 10 |
| Myelomas | 60 ± 20 | 180 ± 25 |
| SLE | | |
| Myesthenia gravis | | B cells producing self reactive ab |
| Rheumatoid arthritis | | Self reactive T lymphocyte |
| Organ Transplantation | | |

What is claimed is:

1. A method of treating an individual having acute myeloid leukemia, acute promyelocytic leukemia, lymphoma or myeloma, comprising the steps of:
   a) administering to said individual a pharmacologically effective dose of a retinoid which up-regulates the expression of CD38 antigen, followed by
   b) administering to the same individual a pharmacologically effective dose of an immunotoxin directed to CD38,
   wherein said retinoid is administered in a dose of from about 0.1 mg/kg to about 2 mg/kg.

2. The method of claim 1, wherein said retinoid is a material selected from the group consisting of all-trans-retinoic acid (RA); 9-cis retinoic acid (9-cis RA); (E) 4[2(5,6,7,8-tetrahydro-5,5,8,8-tetramethyl-2-naphthalenyl)-1-propenyl]benzoic acid (TTNPB); and, (E)-4-[2-(5,6,7,8,-tetrahydro-3,5,5,8,8-pentamethyl-2-naphthalenyl)-1-propenyl]benzoic acid (3-met TTNPB).

3. The method of claim 1, wherein said immunotoxin comprises a monoclonal antibody directed against the CD38 antigen conjugated to a toxin molecule.

4. The method of claim 3, wherein said toxin is gelonin.

5. The method of claim 1, wherein said acute promyelocytic leukemia is adriamycin resistant.

6. A method of treating an individual having acute myeloid leukemia, acute promyelocytic leukemia, lymphoma or myeloma, comprising the steps of:
   a) administering to said individual a pharmacologically effective dose of a retinoid which up-regulates the expression of CD38 antigen, followed by
   b) administering to the same individual a pharmacologically effective dose of an immunotoxin directed to CD38,
   wherein said immunotoxin is administered in a dose of from about 0.05 mg/kg to about 2 mg/kg.

7. The method of claim 6, wherein said retinoid is selected from the group consisting of all-trans-retinoic acid (RA); 9-cis retinoic acid (9-cis RA); (E) 4[2(5,6,7,8-tetrahydro-5,5,8,8-tetramethyl-2-naphthalenyl)-1-propenyl]benzoic acid (TTNPB); and, (E)-4-[2-(5,6,7,8,-tetrahydro-3,5,5,8,8-pentamethyl-2-naphthalenyl)-1- propenyl]benzoic acid (3-met TTNPB).

8. The method of claim 6, wherein said immunotoxin comprises a monoclonal antibody directed against the CD38 antigen conjugated to a toxin molecule.

9. The method of claim 8, wherein said toxin is gelonin.

10. The method of claim 6, wherein said acute promyelocytic leukemia is adriamycin resistant.

* * * * *